US 6,592,733 B1

(12) United States Patent
Foley et al.

(10) Patent No.: US 6,592,733 B1
(45) Date of Patent: Jul. 15, 2003

(54) CAPILLARY ELECTROPHORESIS DEVICES INCORPORATING OPTICAL WAVEGUIDES

(75) Inventors: Barbara Foley, Phoenix, AZ (US); Jaymie Sawyer, Chandler, AZ (US); Cynthia G. Briscoe, Tempe, AZ (US)

(73) Assignee: Motorola, Inc., Schaumburg, IL (US)

( * ) Notice: Subject to any disclaimer, the term of this patent is extended or adjusted under 35 U.S.C. 154(b) by 0 days.

(21) Appl. No.: 09/438,873

(22) Filed: Nov. 12, 1999

(51) Int. Cl.[7] .................. G01N 27/26; G01N 27/447
(52) U.S. Cl. .................. 204/603; 204/452; 250/573; 250/458.1; 356/344
(58) Field of Search .................. 204/603, 452; 356/344; 250/458.1, 459.1, 461.1, 461.2, 573, 575

(56) References Cited

U.S. PATENT DOCUMENTS

| | | | |
|---|---|---|---|
| 5,192,412 A | 3/1993 | Kambara | 204/612 |
| 5,194,915 A | 3/1993 | Gilby et al. | 356/318 |
| 5,292,620 A | 3/1994 | Booth et al. | 430/290 |
| 5,302,272 A | 4/1994 | Klein | 204/603 |
| 5,312,535 A | 5/1994 | Wasks et al. | 204/603 |
| 5,324,401 A | 6/1994 | Yeung et al. | 204/452 |
| 5,413,686 A | 5/1995 | Klein et al. | 204/603 |
| 5,500,071 A | 3/1996 | Kaltenbach et al. | 156/272.8 |
| 5,541,420 A | 7/1996 | Kambara | 204/602 |
| 5,545,901 A | 8/1996 | Pentoney, Jr. et al. | 250/458.1 |
| 5,582,705 A | 12/1996 | Yeung et al. | 204/603 |
| 5,741,411 A | 4/1998 | Yeung et al. | 204/452 |
| 5,741,412 A | 4/1998 | Dovichi et al. | 204/602 |
| 5,763,277 A | 6/1998 | Zhu | 436/172 |
| 5,790,727 A | 8/1998 | Dhadwal et al. | 385/38 |
| 5,867,266 A | 2/1999 | Craighead | 356/344 |
| 5,885,470 A | 3/1999 | Parce et al. | 216/33 |
| 5,898,493 A | 4/1999 | Jankowiak et al. | 356/318 |
| 5,900,934 A | 5/1999 | Gilby et al. | 356/344 |
| 5,935,401 A | 8/1999 | Amigo | 204/454 |
| 5,938,908 A | 8/1999 | Anazawa et al. | 204/603 |
| 5,942,443 A | 8/1999 | Parce et al. | 436/514 |
| 5,954,931 A | 9/1999 | Maracas et al. | 204/451 |
| 6,437,345 B1 * | 8/2002 | Bruno-Raimondi et al. | 250/458.1 |
| 6,438,279 B1 * | 8/2002 | Craighead et al. | 385/12 |

FOREIGN PATENT DOCUMENTS

| | | |
|---|---|---|
| EP | 0581413 A2 | 2/1994 |
| GB | 2312505 A | 10/1997 |
| JP | 0854362 A2 | 1/1998 |
| WO | WO 94/18552 A1 | 8/1994 |
| WO | WO 98/10122 A1 | 3/1998 |
| WO | WO 98/22799 A2 | 5/1998 |
| WO | WO 98/23945 A1 | 6/1998 |
| WO | WO 99/37996 A1 | 7/1999 |

OTHER PUBLICATIONS

J.R. Wendt, M.E. Warren, W.C. Sweatt, C.G. Bailey, C.M. Matzke, D.W. Arnold, A.A. Allerman, T.R. Carter, R.E. Asbill, and S. Samora, The 43rd International Conference on Electron, Ion and Photon Beam Technology and Nanofabrication, Abstracts, "Fabrication of High Performance Microlenses for an Intergrated Capillary Channel Electrochromatograph with Flourescence Detection", Jun. 1–4, 1999, 3 pages.

D.J. Harrison and N. Chiem, "Immunoassay Flow System on Chip" Seventh IEEE Solid—State Sensor and Actuator Workshop, Jun. 3–6, 1996, p. 3–6.

* cited by examiner

Primary Examiner—Nam Nguyen
Assistant Examiner—John S. Starsiak, Jr.
(74) Attorney, Agent, or Firm—Douglas W. Gilmore

(57) ABSTRACT

A capillary electrophoresis device having a substrate layer and a cover layer, with a plurality of electrophoresis channels formed in the substrate layer, includes an optical waveguide system that transmits excitation radiation from a source port into each one of the electrophoresis channels. The optical waveguide system is defined by regions, within either the cover or substrate, that have an index of refraction higher than that of the surrounding material.

5 Claims, 4 Drawing Sheets

200

CAPILLARY ELECTROPHORESIS DEVICES INCORPORATING OPTICAL WAVEGUIDES

BACKGROUND OF THE INVENTION

1. Field of the Invention

This invention relates to the field of capillary electrophoresis. More particularly, this invention relates to capillary electrophoresis devices having optical waveguides that direct excitation radiation to the electrophoresis channels.

2. Description of Related Art

Capillary electrophoresis is an established technique for separating chemical components. A sample solution containing the chemical components to be separated is placed in an electrophoresis channel containing an electrophoretic medium. For example, the electrophoresis channel may be provided by a length of capillary tubing. Upon the application of an electric field along the length of the electrophoresis channel, the different chemical components within the sample migrate at distinct rates towards the oppositely charged end of the capillary, the rate of migration being dependent on the chemical substance's electrophoretic mobility in the electrophoretic medium. As a result of their distinct rates of migration, the various chemical components become separated as they progress along the electrophoresis channel and, thus, can be separately detected.

Various means for detecting the separated chemical components are known. If the chemical components of interest are fluorescent, then they can be conveniently detected by inducing their fluorescence. In particular, many biological components, such as proteins and nucleic acids, even if not themselves fluorescent, can be made fluorescent by conjugating them to any number of fluorophores using well-known techniques. In the induced fluorescence approach, electromagnetic radiation at an excitation wavelength, the wavelength needed to induce fluorescence, is directed to a particular point in the electrophoresis channel. The excitation wavelength is typically in the ultra-violet or visible spectrum, and the source of the excitation radiation is typically a laser. The induced fluorescence radiation may then be detected by a light-sensitive detector, such as a charge-coupled device (CCD), photodiode array, or photomultiplier tube (PMT).

The analytical capacity of capillary electrophoresis techniques is often multiplied by using many electrophoresis channels in parallel. Typically, these multiple electrophoresis channels are arranged in the same plane with their start and finish points aligned. Directing the excitation radiation to each of the electrophoresis channels is more complicated in this geometry, especially since, to allow for parallel detection, it is preferable to apply the excitation radiation to each electrophoresis channel at the same distance from the starting point at the same time.

In one approach that has been used with an array of electrophoresis capillaries, a beam expander and a cylindrical lens are used to focus laser light into a thin line that intersects the axes of the capillaries. A significant disadvantage with this approach, however, is that much of the excitation radiation will be wasted because it will fall between the cores of the capillaries, which is where the components to be detected are located. Moreover, the distribution of intensity along the focussed line will be highly non-uniform, unless the focussed line is much longer than the width of the capillary array, thereby causing even more of the excitation radiation to be wasted.

Optical waveguide systems have also been used to direct the excitation radiation to multiple electrophoresis capillaries. For example, in the systems disclosed in U.S. Pat. Nos. 5,312,535; 5,324,401; and 5,413,686, each electrophoresis capillary is provided with at least one optical fiber that directs the excitation radiation to it. However, such systems become bulky and complex as the number of electrophoresis capillaries becomes large. Moreover, each optical fiber must be carefully aligned with each capillary in order to achieve efficient and uniform illumination of each capillary.

U.S. Pat. No. 5,790,727 discloses a system wherein the capillaries are arranged in a parallel array so that the capillaries themselves act as optical waveguides. In particular, refraction at the cylindrical surfaces of the capillaries confine excitation radiation applied from the side of the array to the core of each capillary in the array. While potentially efficient, this approach requires particularly precise arrangement of the capillaries so that they will form waveguides.

Increasingly, capillary electrophoresis is conducted in microfluidic devices. Instead of using individual capillaries, the electrophoresis channels are provided as microfluidic channels formed into a substrate, such as glass, silicon, or plastic. To allow detection by induced fluorescence, the microfluidic device may include an optically transparent portion so that the excitation radiation can reach the electrophoresis channels. An example is the microfluidic device disclosed in U.S. Pat. No. 5,958,694. However, this device included only a single capillary electrophoresis channel. When microfluidic electrophoresis devices include multiple electrophoresis channels, a similar difficulty in illuminating the multiple channels with the excitation radiation arises, as when discrete capillaries are used.

SUMMARY OF THE INVENTION

The present invention provides a capillary electrophoresis device comprising a substrate and an optical waveguide system. A plurality of electrophoresis channels are formed in the substrate. The optical waveguide system has a source port and a plurality of output port and transmits light entering the source port into each one of the electrophoresis channels through one of the output ports.

DETAILED DESCRIPTION OF THE INVENTION

Figure 1:
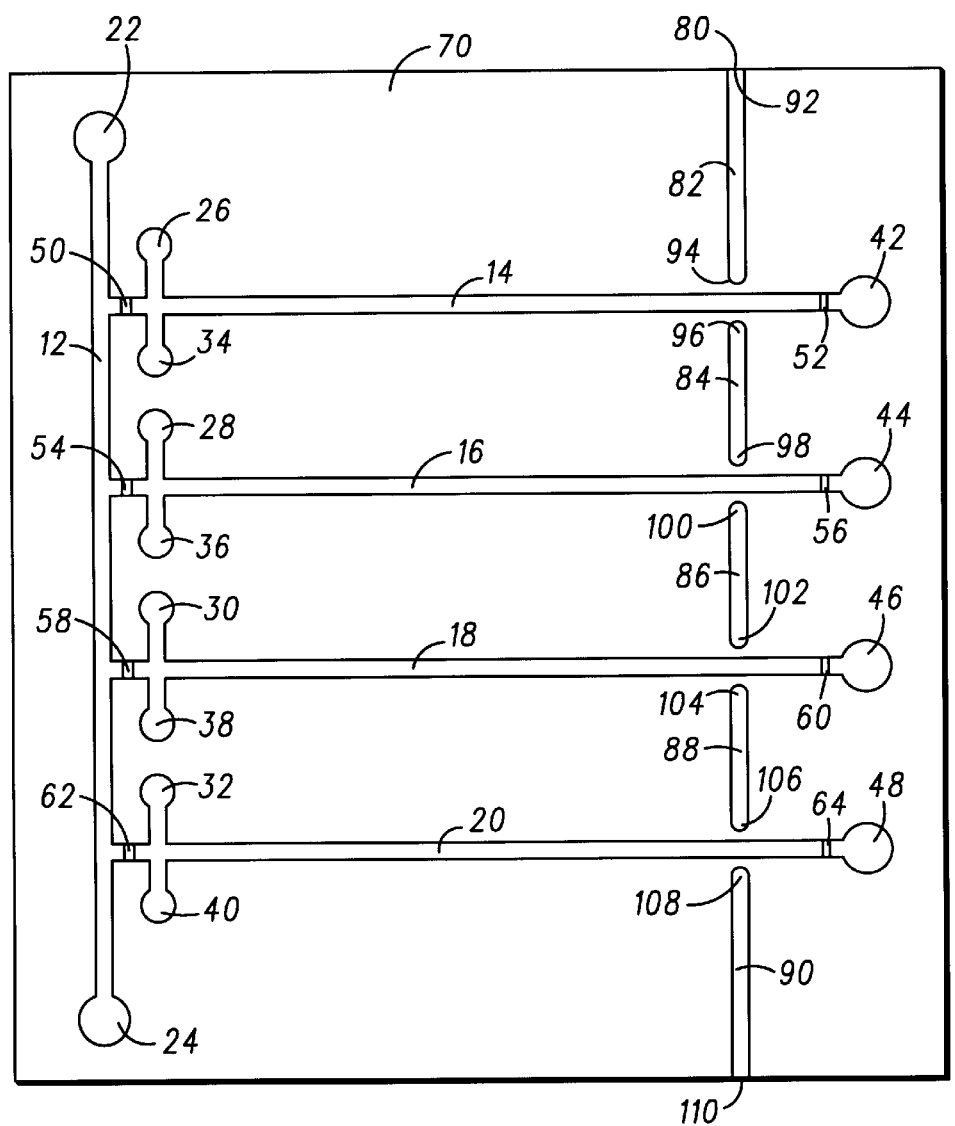
FIG. 1 is a top schematic view of a capillary electrophoresis device, in accordance with a first preferred embodiment of the present invention.

Shown in FIG. 1 is a capillary electrophoresis device 10, in accordance with a first preferred embodiment of the present invention. Electrophoresis device 10 includes a sample channel 12 and electrophoresis channels 14–20 in fluid communication with sample channel 12. Though, for purposed of illustration, capillary electrophoresis device 10 is shown in FIG. 1 with four electrophoresis channels 14–20, device 10 may include a greater or fewer number. Sample channel 12 has a sample input port 22 and a waste output port 24. Electrophoresis channels 14–20 are provided with reagent input ports 26–32, reagent output ports 34–40, and terminate in waste ports 42–48. Disposed in electrophoresis channels 14–20 are electrodes 50–64.

Figure 2:
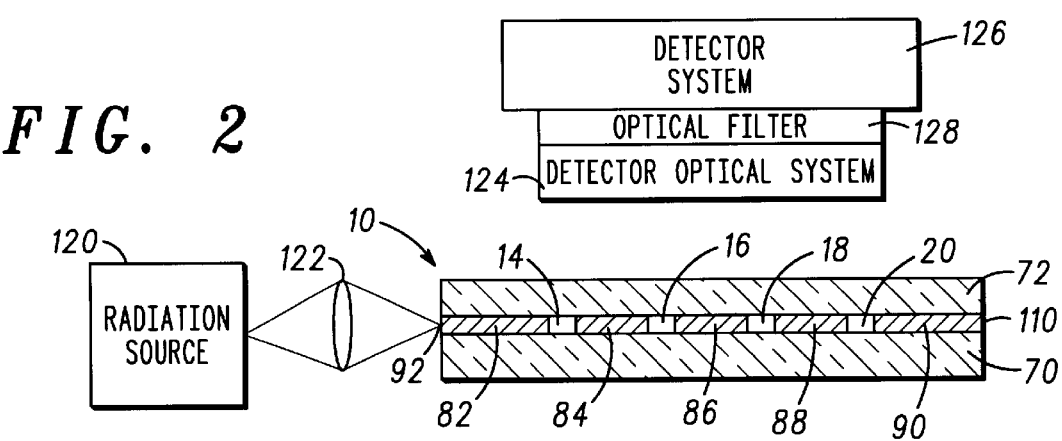
FIG. 2 is a side schematic view of the capillary electrophoresis device of FIG. 1 and of components to deliver excitation radiation to the capillary electrophoresis device and to detect fluorescence radiation from the capillary electrophoresis device, in accordance with a first preferred embodiment of the present invention.

Capillary electrophoresis device 10 is preferably provided as a microfluidic device, in which case device 10 comprises a substrate layer 70 and a cover layer 72, as shown in FIG. 2. Sample channel 12 and electrophoresis channels 14–20 are formed into substrate layer 70. Substrate 70 is a solid material, such as glass, fused silica, silicon, plastic, or ceramic. Channels, 12–20 are typically less than 250 microns wide and are typically about 4 to 5 cm long. When substrate 70 is glass, fused silica, or silicon, channels 12–20 may be formed by well-known microfabrication techniques, such as photolithography, wet etching, micromachining, or laser ablation. When substrate 70 is plastic, channels 12–20 may be conveniently formed by embossing, stamping, or injection molding, in addition to the above-listed techniques. As shown in FIG. 2, channels 14–20 are preferably co-planar.

Cover layer 72 is also made out of a solid material, such as glass, silicon, plastic, or ceramic. Cover layer 72 is attached to substrate 70, so as to seal channels 12–20. Cover 72 may be attached to substrate 70 using various techniques depending on the materials used. As one example, cover 72 may be attached to substrate 70 using an adhesive. The materials of substrate 70 and cover 72 are chosen so that one of the two layers is transparent to the fluorescence radiation from the components to be detected in channels 14–20, as described in more detail below. Additionally, ports 22–48 are provided as holes in either substrate 70 or cover 72.

Electrophoresis device 10 is provided with an optical waveguide system 80 comprising optical waveguide segments 82–90 disposed in substrate layer 70. As used herein, an "optical waveguide" is a component that guides electromagnetic radiation of a given wavelength, which may be in the ultra-violet, visible, or infrared part of the spectrum, along a predetermined path by using total internal reflection to confine the electromagnetic radiation into at least a core part of the component. The total internal reflection occurs in the optical waveguide because the core part has an index of refraction for the given wavelength that is higher than the surrounding material. An optical fiber is an example of a particularly efficient optical waveguide.

With reference to FIGS. 1 and 2, optical waveguide segment 82 includes a source port 92 at the edge of device 10 and an output port 94. Segment 82 transmits the excitation radiation applied at source port 92 to output port 94 and directs the excitation radiation from output port 94 to channel 14. Optical waveguide segment 84 has an input port 96 and an output port 98. Input port 96 collects excitation radiation from channel 14 and directs it via output port 98 to channel 16. Similarly, optical waveguide segment 86 has an input port 100 for collecting excitation radiation from channel 16 and an output port 102 for directing the collected excitation radiation to channel 18; and optical waveguide segment 88 has an input port 104 for collecting excitation radiation from channel 18 and an output port 106 for directing the collected excitation radiation to channel 20. Finally, optical waveguide segment 90 has an input port 108 and an output port 110 at the edge of device 10. Input 108 collects excitation radiation from channel 20 and directs the collected excitation radiation to output port 110. In this way, optical waveguide segments 82–90 of optical system 80 serve to transmit excitation radiation entering input port 92 to channels 14–20 and then to output port 110.

As shown in FIG. 1, output ports 94, 98, 102, and 106 preferably have curved surfaces so as to focus the excitation radiation in channels 14–20, respectively, so that the excitation radiation is delivered to channels 14–20 more efficiently. Additionally, input ports 96, 100, 104, and 108 preferably have curved surfaces so as to collect the excitation radiation from channels 14–20 more efficiently. Alternatively, waveguide segments 82–90 may be provided with microlenses at their input and output ports, instead of having curved input and output ports. Another approach is to have waveguide segments 82–90 extend to the edges of channels 14–20 for more efficient transfer of excitation radiation. Finally, it is also preferable to have channels 14–20 curve toward-each other in order to minimize the lengths of waveguide segments 82–90 and, hence, the losses of excitation radiation in segments 82–90.

Waveguide segments 82–90 may be disposed in substrate 70 in several different ways. In one approach, optical waveguide segments 82–90 may be defined by optical fibers. Channels may be formed in substrate 70 by any of the techniques described above, and the optical fibers may then affixed into the channels, such as by means of adhesive, so as to define segments 82–90.

In another approach, optical waveguide segments 82–90 may be defined by regions where materials have been added to substrate 70, the added materials having an index of refraction that is higher than that of the surrounding substrate 70. For example, channels of the appropriate shape may be formed into substrate 70, as described above. The channels are then filled with a material either liquid or solid, that has an index of refraction higher than that of substrate 70, so as to define segments 82–90. In this way, total internal reflection will occur within segments 82–90 so that they function as optical waveguides.

Preferably, however, optical waveguide segments 82–90 are integrally formed in substrate 70. In particular, waveguide-forming materials are available in which light may be used to selectively polymerize monomers in the material, so that the resulting photopolymerized regions have an index of refraction that is higher than the surrounding regions. In this way, a pattern of light can be used to define an optical waveguide pattern in polymeric, i.e., plastic materials. Such waveguide-forming materials may comprise acrylate and methacrylate monomers in a polymer binder and may also include initiators and other constituents. Further details are provided in U.S. Pat. No. 5,292,620, which is fully incorporated herein by reference. Such waveguide-forming materials are commercially available from Polymer Photonics, Inc., Kennett Square, Pa. under the trademark POLYGUIDE.

Thus, substrate 70 is preferably a waveguide-forming polymeric composition, in which optical waveguide segments 82–90 have been integrally formed by exposure to light in an appropriate pattern. Channels 12–20 may be formed into substrate 70 as described above, either before or after waveguide segments 82–90 are formed. If necessary, the surfaces of electrophoresis channels 14–20 can be modified to acquire the surface charge profile needed for capillary electrophoresis. Such surface modification can be accomplished by providing an anchoring polymer layer that interpenetrates the surfaces of electrophoresis channels 14–20 and an electrophoretic polymer layer copolymerized with the anchoring polymer layer. This surface modification technique is described in U.S. Pat. No. 5,935,401, which is fully incorporated herein by reference.

Capillary electrophoresis device 10 may be used in the following way. Before receiving the sample to analyzed, electrophoresis channels 14–20 are filled with an electrophoresis medium, such as a polyacrylamide gel. A sample solution is introduced into sample input port 22 so that it fills up channel 12. Reagents may be introduced into channels 14–20 through reagent input ports 26–22, respectively. The reagents may be chemical substances that react with certain components suspected of being present in the sample. For example, the reagents may include antigens that bind with certain antibodies, so as to detect the presence of certain antibodies in the sample. The reagents introduced into reagent input ports 26–22 may all be the same, or they may be different. The chemical components should be fluorescent in order to be detected. The fluorescent components to be detected may be present in either the reagents or the sample, or may result from the reaction of the reagents With components in the sample.

Voltages are applied to electrodes 50–64, thereby creating electric fields along the lengths of channels 14–20. Typically, the voltages applied to electrodes 50–64 are sufficient to apply between about 175 V/cm and 250 V/cm across each of channels 14–20. The electric fields created by electrodes 50–64 cause the chemical components in each of channels 14–20 to migrate toward waste ports 42–48, respectively, and to separate. During this migration process, excitation radiation is applied to channels 14–20 and the fluorescence radiation from channels 14–20 is monitored, typically in real time. With reference to FIG. 2, a source 120, which is preferably a laser, produces the excitation radiation at the desired wavelength. A source optical system 122 couples the excitation radiation into optical waveguide system 80 through source port 92. Optical waveguide system 80 transmits the excitation radiation to each of channels 14–20, as described above. A detector optical system 124 images the fluorescence radiation from channels 14–20 onto a detector system 126. Detector system 126 preferably includes a multi-channel detector, such as a charge-coupled device (CCD) or photodiode array, so that the fluorescence radiation from each of channels 14–20 may be monitored individually. Preferably, an optical filter 128 is used to block the wavelengths corresponding to the excitation radiation and to pass to detector system 126 the wavelengths corresponding to the fluorescence radiation. Alternatively, detector system 126, along with filter 128, may be placed close enough to device 10 that detector optical system 124 is not needed.

After the electrophoretic separation and detection has been completed, the materials remaining in device 10 can be removed through waste ports 24–48.

In the configuration shown in FIGS. 1 and 2, the excitation radiation will become attenuated with each successive channel, so that channel 20 will be illuminated with excitation radiation at lower intensity than channel 14. Accordingly, for the same amount of fluorescent material, less fluorescent radiation will emanate from channel 20 than from channel 12. To make up for this difference, channels 14–20 may be provided with differing amounts of fluorescent material, with channel 20 being provided with more fluorescent material than channel 14.

Figure 3:
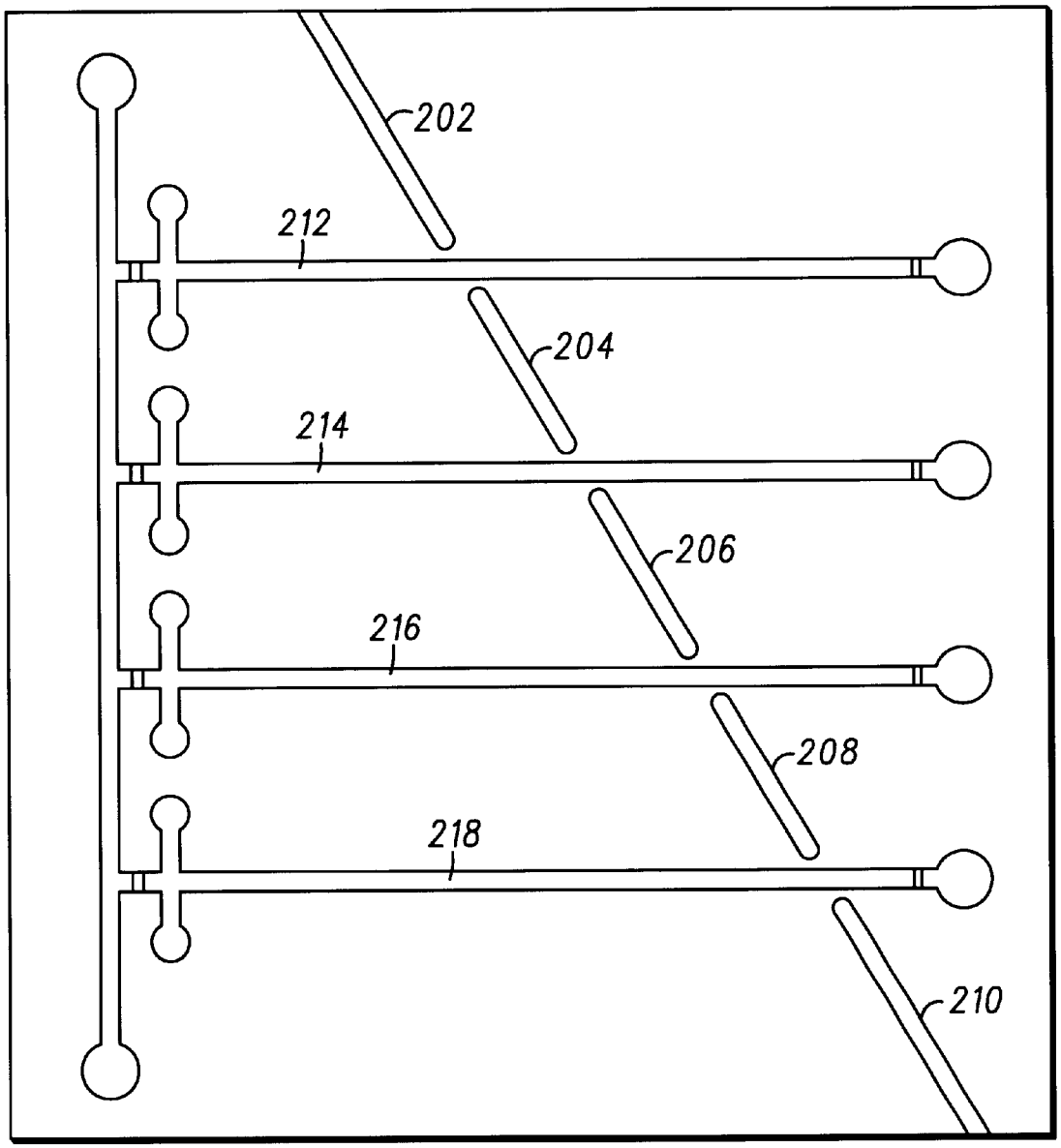
FIG. 3 is a top schematic view of a capillary electrophoresis device, in accordance with a second preferred embodiment of the present invention.

Other arrangements of optical waveguide segments may, also be provided in the electrophoresis devices. For example, shown in FIG. 3 is an electrophoresis device 200 in which optical waveguide segments 202–210 are arranged other than perpendicularly to electrophoresis channels 212–218. In this way, fluorescent components will be detected at different distances along the lengths of channels 212–218.

Electrophoresis device 300, shown in FIG. 3, has yet another arrangement of optical waveguide segments. Optical waveguide segments 302–316 are arranged to define two Y-junctions. Specifically, optical waveguide segment 302 is arranged to transmit excitation radiation from a source port 318 to an electrophoresis channel 320. Waveguide segments 304 and 306 collect excitation radiation from electrophoresis channel 320 and transmit the collected radiation to an electrophoresis channel 322 at points 324 and 326, respectively. Waveguide segments 308 and 310, in turn, collect excitation from channel 322 at points 324 and 326, respectively, and transmit the collected radiation to a electrophoresis channel 328 at points 330 and 332, respectively. Waveguide segments 312 and 314 collect the excitation radiation from channel 328 at points 330 and 332, respectively, and transmit the collected radiation to the same point on an electrophoresis channel 334. Finally, waveguide segment 316 collects excitation radiation from channel 334 and transmits it to an output port 336 at the edge of device 300. In this way, waveguide segments 302–316 are able to transmit excitation radiation to more than one point on electrophoresis channels 322 and 328, so that fluorescence radiation may be monitored from more than one point on channels 322 and 328.

Figure 4:
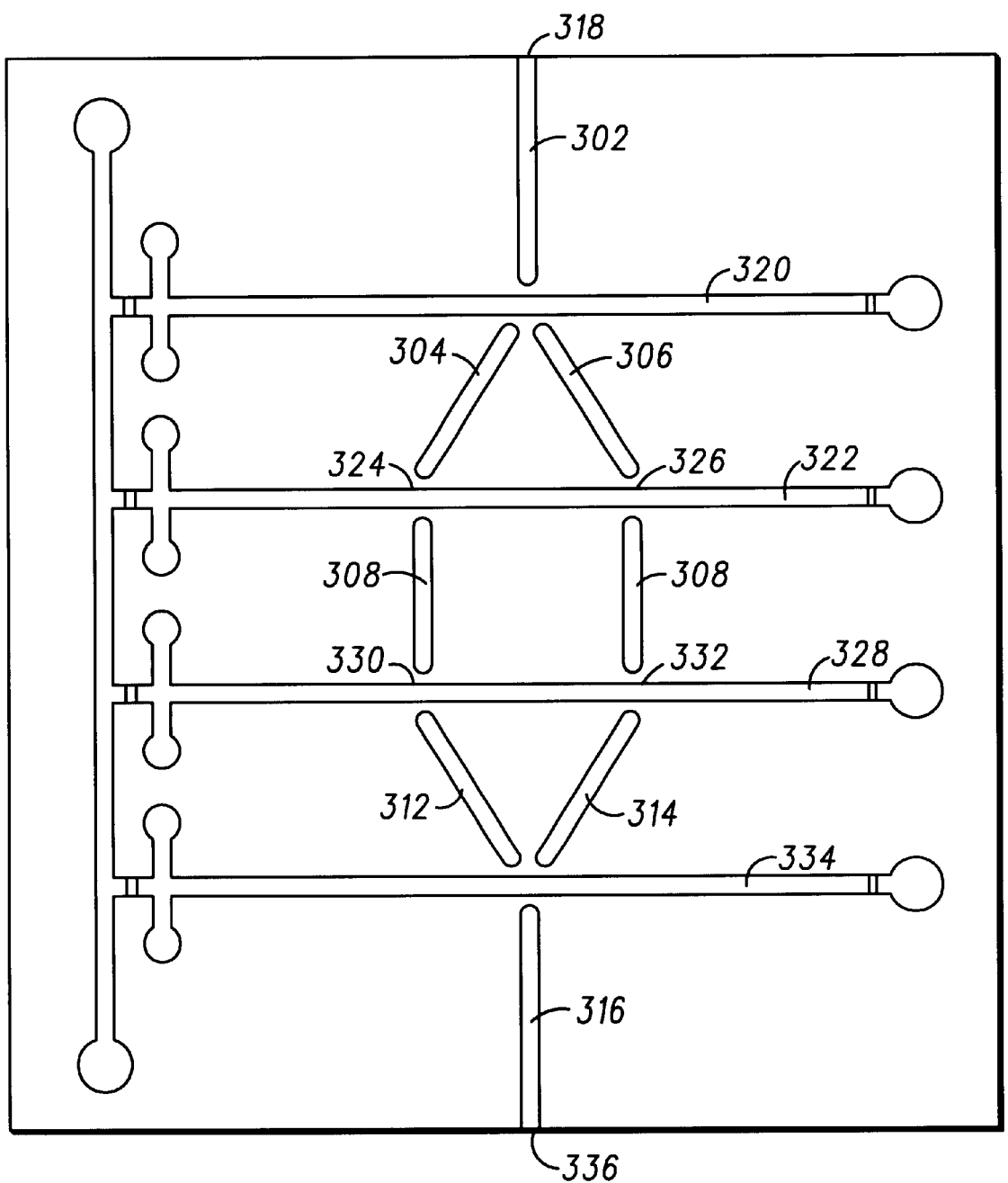
FIG. 4 is a top schematic view of a capillary electrophoresis device, in accordance with a third preferred embodiment of the present invention.
Figure 5:
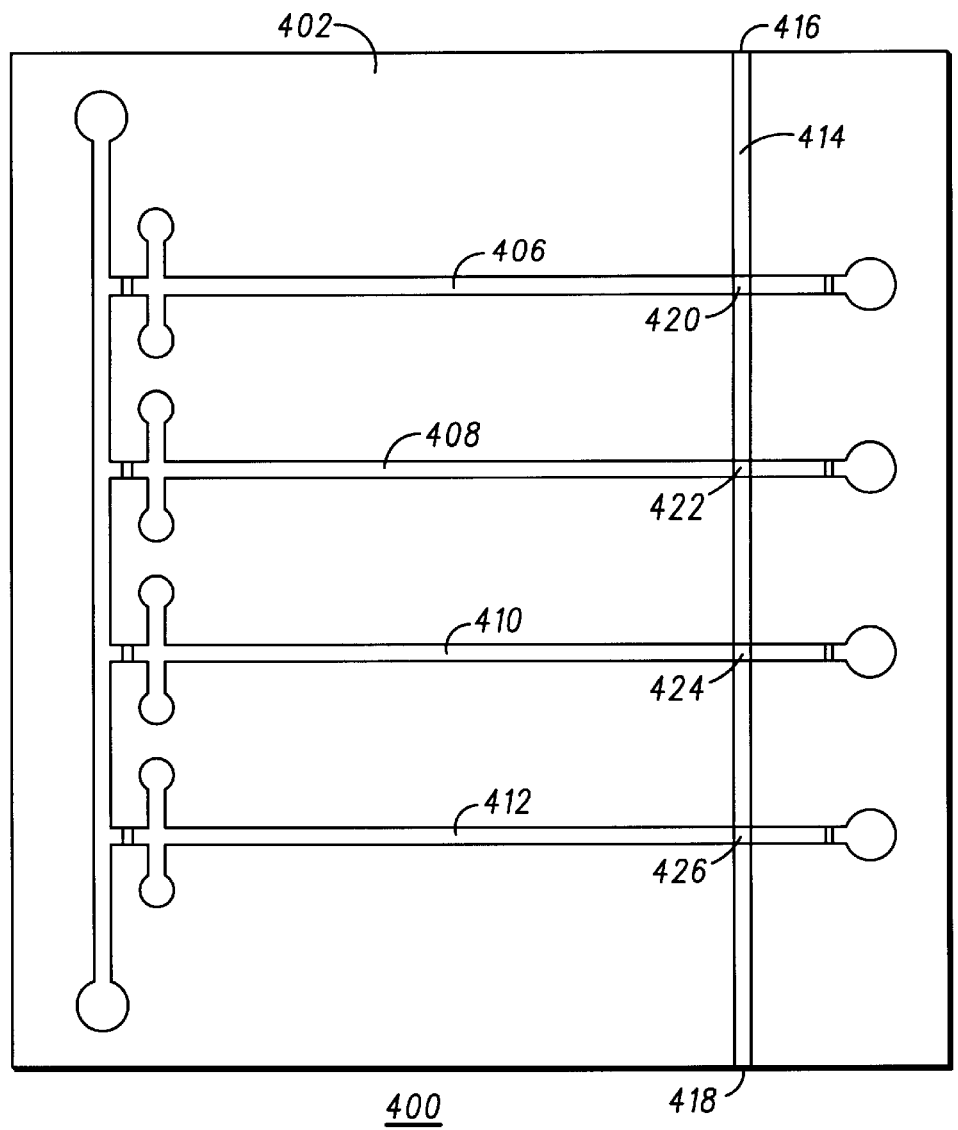
FIG. 5 is a top schematic view of a capillary electrophoresis device, in accordance with a fourth preferred embodiment of the present invention.
Figure 6:
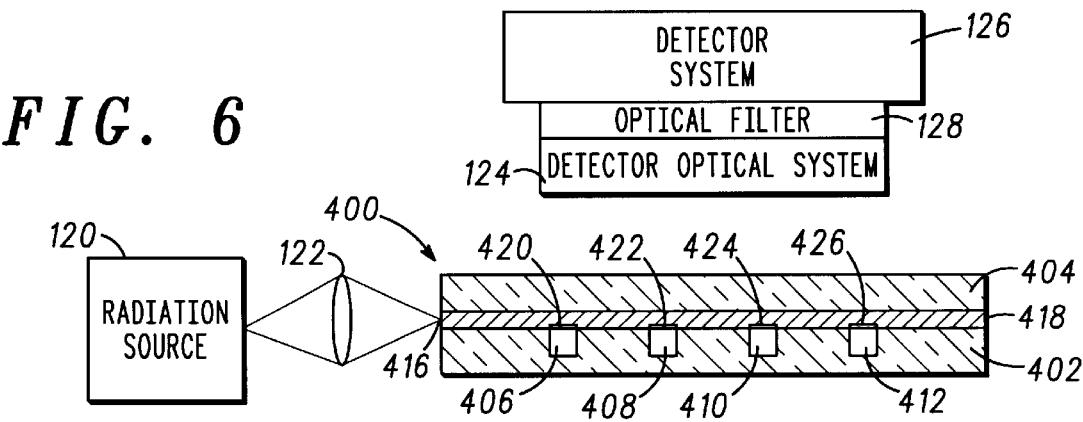
FIG. 6 is a side schematic view of the capillary electrophoresis device of FIG. 5 and of components to deliver excitation radiation to the capillary electrophoresis device and to detect fluorescence radiation from the capillary electrophoresis device, in accordance with a fourth preferred embodiment of the present invention.

Capillary electrophoresis devices 10, 200, and 200, shown in FIGS. 1, 3, and 4 are intended to be illustrative rather than exhaustive of the arrangements optical waveguide segments that may be provided in the device. In general, optical waveguide segments may be arranged in nearly any desired pattern to apply transmit the excitation to desired points on the electrophoresis channels.

in the embodiments shown in FIGS. 1–4, the optical waveguide system was in the same plane as the electrophoresis channels. However, the optical waveguide system may also be in a different plane. With reference to FIGS. 5 and 6, a capillary electrophoresis device 400 comprises a substrate layer 402 and a cover layer 404, attached to substrate layer 402. Electrophoresis channels 406–412 are formed into substrate layer 402. An optical waveguide 414 is formed into cover 404. Optical waveguide 414 has a source port 416 at one edge of device 400 and an output port 418 at another edge of device 400. Optical waveguide 414 is also provided with output ports 420–426 that serve to optically couple waveguide 414 to channels 406–412, respectively. Output ports 420–426 are conveniently provided as diffraction gratings. Preferably, cover 404 is made out of a waveguide-forming material, such as POLYGUIDE, so that optical waveguide 414 is formed by photopolymerizing the desired areas of cover 404, as described above. Moreover, when materials such as POLYGUIDE are used, output ports 420–426 may be conveniently provided as diffraction gratings. The diffraction gratings can be produced holographically by interfering lasers, as described in U.S. Pat. No. 5,292,620, incorporated herein by reference.

With reference to FIG. 6, excitation radiation from source 120 may be coupled into input port 416, via source optical system 122. Optical waveguide 414 transmits the excitation radiation from input port 416 to channels 406–412, via output ports 420–426. Fluorescence radiation from channels 406–412 is imaged onto detector system 126 by detector optics 124, and optical filter 128 is used to block the wavelengths corresponding to the excitation radiation and to pass the wavelengths corresponding to the fluorescence radiation.

Although various embodiments have been shown and described herein, it should be understood that various modifications and substitutions, as well, as rearrangements and combinations of the preceding embodiments, can be made be made by those skilled in the art, without departing from the novel spirit and scope of this invention.

What is claimed is:

1. A capillary electrophoresis devise comprising:

a substrate, said substrate having a plurality of electrophoresis channels formed therein;

an optical waveguide system having at least one of a source port and a plurality of output ports, wherein said optical waveguide system is suitably adapted to effectively transmit light entering said source port into each of said electrophoresis channels through at least one of said output ports;

said optical waveguide system further comprising at least one of a source segment and a plurality of intermediate segments, said source segment comprising at least one of said source port and one of said output ports, each one of said intermediate segments comprising at least one of an input port and one of said output ports, wherein each one of said input ports is suitably adapted to effectively receive light transmitted substantially through one of said electrophoresis channels by at least one of said output ports; and each one of said output ports suitably shaped so as to focus light in at least one of said electrophoresis channels.

2. The capillary electrophoresis device of claim 1, wherein each of said input ports is suitably shaped so as to effectively gather light substantially focused by at least one of said output ports.

3. A capillary electrophoresis device comprising:

a substrate, said substrate having a plurality of electrophoresis channels formed therein;

an optical waveguide system having at least one of a source port and a plurality of output ports, wherein said optical waveguide system is suitably adapted to effectively transmit light entering said source port into each of said electrophoresis channels through at least one of said output ports; and a cover attached to said substrate, at least a portion of said optical waveguide system being disposed in said cover.

4. The capillary electrophoresis device of claim 3, wherein said optical waveguide system is substantially integral with said cover, said optical waveguide system at least partially defined by suitably high index of refraction regions substantially within said cover.

5. The capillary electrophoresis device of claim 4, wherein at least one of said output ports comprises a grating.

* * * * *

UNITED STATES PATENT AND TRADEMARK OFFICE
CERTIFICATE OF CORRECTION

PATENT NO. : 6,592,733 B1
DATED : July 15, 2003
INVENTOR(S) : Barenburg et al.

It is certified that error appears in the above-identified patent and that said Letters Patent is hereby corrected as shown below:

Column 8,
Line 6, after "in at least" add -- one --.

Signed and Sealed this

Fourth Day of May, 2004

JON W. DUDAS
*Acting Director of the United States Patent and Trademark Office*